United States Patent [19]

Fang

[11] Patent Number: 5,426,196
[45] Date of Patent: Jun. 20, 1995

[54] SYNTHESIS OF DIARYL METHANES
[75] Inventor: Francis G.a Fang, Durham, N.C.
[73] Assignee: Glaxo Inc., Research Triangle Park, N.C.
[21] Appl. No.: 173,289
[22] Filed: Dec. 22, 1993
[51] Int. Cl.$^6$ ................ C07C 29/143; C07C 319/02; C07D 307/83
[52] U.S. Cl. .................... 549/307; 544/283; 546/152; 548/262.4; 548/304.4; 548/361.1; 549/58; 549/471; 568/67; 568/809
[58] Field of Search .............. 549/307; 568/67, 809

[56] References Cited

U.S. PATENT DOCUMENTS

| | | | |
|---|---|---|---|
| 4,978,672 | 12/1990 | Bowman et al. | 514/383 |
| 5,190,959 | 3/1993 | Murai et al. | 514/318 |

FOREIGN PATENT DOCUMENTS

| | | |
|---|---|---|
| 2057338 | 6/1992 | Canada . |
| 0257171A | 3/1988 | European Pat. Off. . |
| 0316097A | 5/1989 | European Pat. Off. . |
| 0458160A2 | 11/1991 | European Pat. Off. . |
| 0578847A1 | 1/1994 | European Pat. Off. . |
| WO93/25548 | 12/1993 | WIPO . |

OTHER PUBLICATIONS

March, Advanced Organic Chemistry, Third Edition, John Wiley & Sons, New York (1985) pp. 994–995.
Mitsunobu, O., The Use of Diethyl Azodicarboxylate and Triphenylphosphine in Synthesis and Transformation of Natural Products, *Synthesis*, 1–28, Jan. 1981.
Davis, R., et al., 2,4-Dimethylbenzyl: A Compliant Phenol Protecting Group, *Synthesis*, 987–88, Nov. 1982.
Adam, S., An Expedient and High Yielding Synthesis of Mefloquine, via Fluoride Ion-Catalyzed Wittig Rearrangement I, Tetrahedron, vol. 45, No. 5, 1409–14, 1989.

*Primary Examiner*—Richard L. Raymond
*Attorney, Agent, or Firm*—Charles E. Dadswell

[57] ABSTRACT

The present Invention includes synthetic steps and intermediates involved in the following reaction scheme a of converting compounds of Formula (II) to the diarylmethanes of Formula (I):

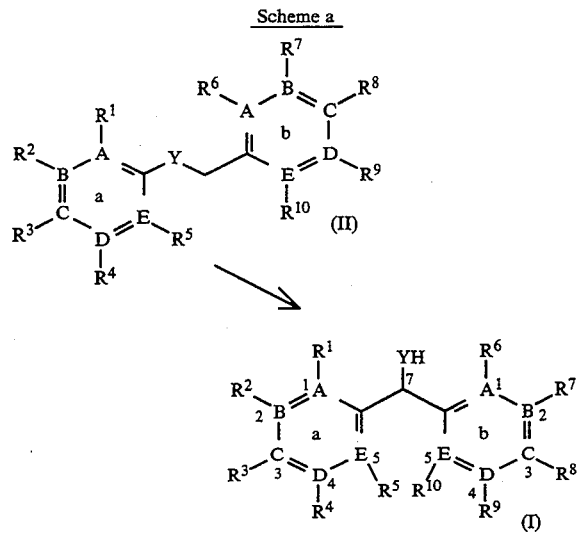

wherein:
Y is oxygen or sulfur;
A, B, C, D, and E are carbon or 1, 2 or 3 of A, B, C, D, and E are independently nitrogen, and the others are carbon; and wherein
$R^1$ through $R^{10}$ are selected independently from the group consisting of: hydrogen, hydroxy, alkyl, $C_3$–$C_8$ cycloalkyl, $C_3$–$C_8$ cycloalkyl alkyl, alkenyl, hydroxy alkyl, alkoxy alkyl, perhalo-alkyl, amino, nitro, nitrile, halo, carboxyl, sulfonyl, acyl, formyl, carbamoyl, trifluoromethyl, aminomethyl, azido, amido, hydrazino, aryl, aryloxy, heteroaryl, or aryl or heteroaryl, mono, di, or tri substituted with one or more hydrogen, hydroxy, alkyl, $C_3$–$C_8$ cycloalkyl, $C_3$–$C_8$ cycloalkyl alkyl, alkenyl, hydroxy alkyl, alkoxy alkyl, perhaloalkyl, amino, nitro, nitrile, halo, carboxyl, sulfonyl, acyl, formyl, carbamoyl, trifluoromethyl, aminomethyl, azido, amido, hydrazino, aryl, aryloxy, or heteroaryl groups and;

the pharmaceutically acceptable salts and solvates thereof.

6 Claims, No Drawings

SYNTHESIS OF DIARYL METHANES

BACKGROUND OF THE INVENTION

Diaryl methanes are useful as intermediates in the formation of many beneficial pharmaceutical compounds. Examples include: antihistamines, such as triprolidine and acrivastine, thromboxane synthetase inhibitors, such as furegrelate, gastric antisecretory agents, such as fenoctimine, nonsedative antidepressants, such as sertraline, antiarrhythmic agents, such as cibenzoline, topical antifungals, such as bifonazole, antimalarials, such as enpiroline, nonsteroidal antiinflammatory agents, such as bromfenac, diuretics such as brocrinat, anthelminitics, such as etibendazole and anticancer compounds, such as tamoxifen and numerous aromatase inhibitors. Examples of these can be found in 4 D. Lednicer, L. Mitscher and G. Georg, *Organic Chemistry of Drug Synthesis* 105, 125-35 (1990); U.S. Pat. No. 4,978,672 to Bowman et al., issued Dec. 18, 1990; and European Patent Application 0 458 160 A2, filed by Sociedad Espanola De Especialidades Farmaco-Terapeuticas, A. A. Avda., published Nov. 27, 1991.

SUMMARY OF THE INVENTION

The present Invention includes synthetic steps and intermediates involved in the following reaction scheme a of converting compounds of Formula (II) to the diarylmethanes of Formula (I):

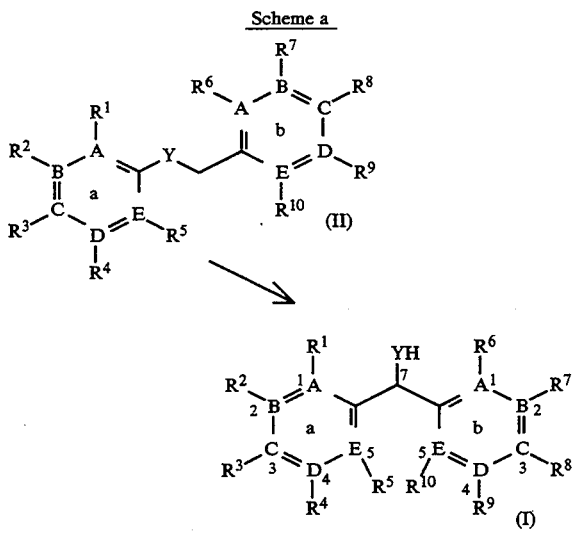

wherein:
Y is oxygen or sulfur;
A, B, C, D, and E are carbon or 1, 2 or 3 of A, B, C, D, and E are independently nitrogen, and the others are carbon; and
wherein
$R^1$ through $R^{10}$ are selected independently from the group consisting of: hydrogen, hydroxy, alkyl, $C_3$-$C_8$ cycloalkyl, $C_3$-$C_8$ cycloalkyl alkyl, alkenyl, hydroxy alkyl, alkoxy alkyl, perhalo-alkyl, amino, nitro, nitrile, halo, carboxyl, sulfonyl, acyl, formyl, carbamoyl, trifluoromethyl, aminomethyl, azido, amido, hydrazino, aryl, aryloxy, heteroaryl, or aryl or heteroaryl, mono, di, or tri substituted with one or more hydrogen, hydroxy, alkyl, $C_3$-$C_8$ cycloalkyl, $C_3$-$C_8$ cycloalkyl alkyl, alkenyl, hydroxy alkyl, alkoxy alkyl, perhaloalkyl, amino, nitro, nitrile, halo, carboxyl, sulfonyl, acyl, formyl, carbamoyl, trifluoromethyl, aminomethyl, azido, amido, hydrazino, aryl, aryloxy, or heteroaryl groups and;
the pharmaceutically acceptable salts and solvates thereof.

DETAILED DESCRIPTION OF THE INVENTION

As used herein, the term "alkyl", alone or in combination, as used herein means a linear or branched chain saturated hydrocarbon group from $C^1$-$C^{15}$. Exemplary alkyl groups include methyl, ethyl, n-propyl, isopropyl, isobutyl, n-butyl, n-hexyl, and the like. "Alkenyl", alone or in combination, as used herein means a linear or branched chain monounsaturated hydrocarbon group from $C^1$-$C^{15}$. As used herein, the term "alkoxy", alone or in combination, means an alkyl group, as defined above attached through an oxygen atom to the parent molecular subunit. Exemplary alkoxy groups include methoxy, ethoxy, n-propoxy, isopropoxy, isobutoxy, n-butoxy, and the like. Aryl includes phenyl, naphthyl, and phenanthryl. Hetero-aryl includes pyridinyl, pyrimidinyl, furanyl, pyrollyl and thiophenyl. The terms "halo" and "halogen" as used herein means a substitutent which may be fluoro, chloro, bromo, or iodo. The term "cyclic" as used herein means alicyclic, aromatic or heterocyclic. The term "perhalo" as used herein means a substitutent completely saturated with halogens. Exemplary perhalo groups include trifluromethyl or pentafluroethyl. The designation "°C." as used herein means degrees centigrade. The term "room temperature" means from about 20° C. to about 30° C.

Those skilled in the art will recognize that stereocenters exist in compounds of Formula (I). Accordingly, the present invention includes all possible stereoisomers and geometric isomers of Formula (I). For example, where the compound of Formula (I) has an asymmetric carbon atom, such as at position 7, two enantiomeric forms ("R" and "S" configurations) are possible. Thus, the present invention is intended to include both enantiomeric forms and any combinations of these forms and where no specific configuration is depicted at the site of an assymmetric carbon, it is to be understood that both enantiomeric forms and mixtures thereof are represented.

Where a compound of Formula (I) is desired as a single enantiomer, it may be obtained either by resolution of the final product or by stereoselective synthesis from either an isomerically pure starting material or any appropriate intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen.

Alternatively, the compound of Formula I may be directly obtained in an enantioselective process from the compound of Formula II by use of an appropriate chiral nonracemic alkali metal amide base.

Additionally, in situations where tautomers of the compounds of Formula (I) are possible, the present invention is intended to include all tautomeric forms of the compounds. Also included in the invention are other forms of the compound of Formula (I), such as, acids, bases, salts, solvates, polymorphs and the like.

The protecting groups used in the preparation of compounds of Formula (I) may be used in conventional manner. See for example, *Protective Groups in Organic Chemistry* Ed. J. F. W. McOmie (Plenum Press 1973) or *Protective Groups in Organic Synthesis* by Theodora w. Greene (John Wiley and Sons 1981), both incorporated herein by reference.

Conventional amino protecting groups may include, for example, aralkyl groups such as benzyl, diphenylmethyl and triphenylmethyl groups or acyl groups such as N-benzyloxycarbonyl or t-butoxycarbonyl. Thus, compounds of Formula (I) wherein one or more of the groups $R^1$ through $R^{10}$ represent hydrogen may be prepared by deprotection of a corresponding protected compound.

Hydroxy groups may be protected, for example, by aralkyl groups, such as benzyl, diphenylmethyl or triphenylmethyl groups; acyl groups such as acetyl and pivaloyl, silicon protecting groups such as trimethylsilyl or t-butyl dimethylsilyl; or as tetrahydropyran derivatives.

Removal of any protecting groups present may be achieved by conventional procedures. For example, an aralkyl group such as benzyl may be cleaved by hydrogenolysis in the presence of a catalyst (e.g. palladium on charcoal) An acyl group such as N-benzyloxycarbonyl may be removed by hydrolysis with, for example, hydrogen bromide in acetic add or by a reduction reaction such as catalytic hydrogenation. Silicon protecting groups may be removed, for example, by treatment with fluoride ion or by hydrolysis under acidic conditions. Tetrahydropyran groups may be cleaved by hydrolysis under acidic conditions.

The present Invention includes synthetic steps and intermediates involved in the following reaction scheme a of converting compounds of Formula (II) to the diarylmethanes of Formula (I):

wherein:

Y is oxygen or sulfur;

A, B, C, D, and E are carbon or 1, 2 or 3 of A, B, C, D, and E are independently nitrogen, and the others are carbon; and wherein $R^1$ through $R^{10}$ are selected independently from the group consisting of: hydrogen, hydroxy, alkyl, $C_3$-$C_8$ cycloalkyl, $C_3$-$C_8$ cycloalkyl alkyl, alkenyl, hydroxy alkyl, alkoxy alkyl, perhalo-alkyl, amino, nitro, nitrile, halo, carboxyl, sulfonyl, acyl, formyl, carbamoyl, trifluoromethyl, aminomethyl, azido, amido, hydrazino, aryl, aryloxy, heteroaryl, or aryl or heteroaryl, mono, di, or tri-substituted with one or more hydrogen, hydroxy, alkyl, $C_3$-$C_8$ cycloalkyl, $C_3$-$C_8$ cycloalkyl alkyl, alkenyl, hydroxy alkyl, alkoxy alkyl, perhalo-alkyl, amino, nitro, nitrile, halo, carboxyl, sulfonyl, acyl, formyl, carbamoyl, trifluoromethyl, aminomethyl, azido, amido, hydrazino, aryl, aryloxy, or heteroaryl groups and;

the pharmaceutically acceptable salts and solvates thereof.

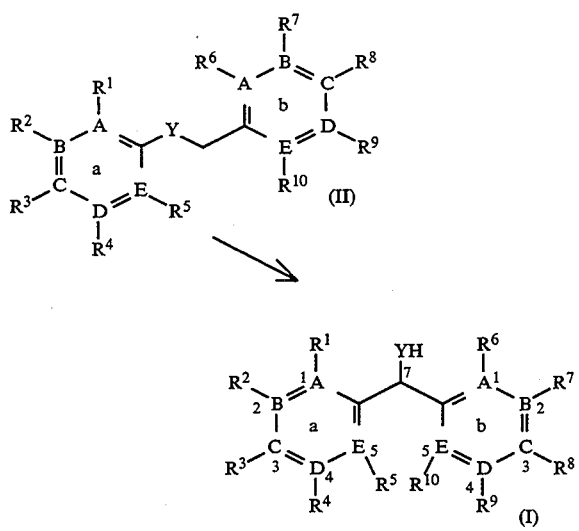

Scheme a

Adjacent substitutents (i.e. substitutents in the 1-2, 2-3, 3-4 or 4-5 positions) on either the "a" ring or "b" ring may be joined together to form a fused ancillary 5 or 6 atom carbocyclic or heterocyclic ring structure. Examples include cyclopentyl, cyclohexyl, cyclohexenyl, furanyl, pyridinyl, phenyl, pyrimidinyl and particularly furanonyl, triazolyl, pyrazolyl, imidazolyl. Substitutents on the and ring structure may each independently be as represented for $R^1$ through $R^{10}$ in conjunction with scheme a above.

The compounds of Formula I are produced in accordance with Scheme a, above wherein: the ether of Formula II is converted to a diarylmethane of Formula I. The ether of Formula II is treated with an alkali metal amide base or alkali metal alkoxy base such as potassium tert-butoxide, lithium diisopropylamide, or particularly sodium hexamethyldisilazide, in a polar aprotic solvent at a temperature of from about $-78°$ C. to about $50°$ C. and stirred for from about 0.5 hours to about 6 hours. The reaction mixture is neutralized with an aqueous acid such as 1N hydrochloric acid and the product is isolated by extractive workup to provide the rearranged diarylmethane of Formula I.

The starting compounds of Scheme a, the compounds of Formula (II), are prepared in accordance with scheme b below wherein:

$R^1$, through $R^{10}$ and Y are as represented in conjunction with Scheme a above;

$R^{11}$ and $R^{12}$ are alkyl or aryl; and

X is chloro, bromo, iodo, hydroxy, methansulfonyloxy, toluenesulfonyloxy or triflurome thanesulfonyloxy.

Scheme b

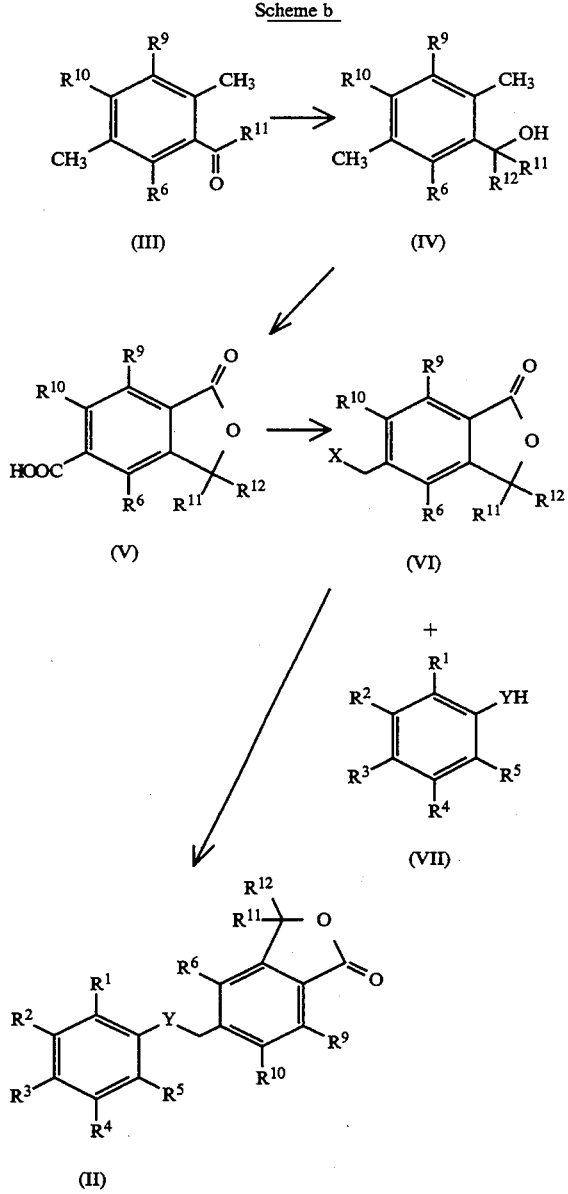

In Scheme b, above, an ether of Formula (II) may be obtained from a substituted arylketone of Formula III. The substituted arylketone of Formula III is converted to a substituted aryldialkylcarbinol of Formula IV by the addition of an organometallic reagent. The reaction is run by adding an alkyllithium or alkylmagnesium halide to the substituted arylketone of Formula III in an aprotic solvent such as tetrahydrofuran, 1,2-dimethoxyethane, diethyl ether, methyl t-butyl ether at a temperature of from about −78° C. to about room temperature for about 1 hour to about 12 hours. The reaction is quenched by pouring the mixture into an acidic medium such as 1N hydrochloric acid or saturated ammonium chloride solution and is isolated by extractive workup to provide the compound of Formula IV. The compound of Formula IV is converted to an isobenzofuranone carboxylic acid of Formula V by oxidizing the aromatic methyl groups to carboxylic acids as described in G. A. Artamkina, et al. *Zh. Org. Khim.* 1980, 16, 698–702 and herein incorporated by reference. The compound of Formula IV is treated with a strong oxidizing agent such as sodium dichromate, selenium dioxide, manganese dioxide, or particularly potassium permanganate and a phase-transfer catalyst such as cetyltrimethylammonium bromide in a polar solvent such as pyridine or particularly water at a temperature of from about room temperature to about 300° C. for a period of from about 1 hour to about 12 hours. The precipitated oxidizing reagent is filtered off. The filtrate is brought to a pH of about 1 and the resultant precipitate is collected by filtration to give the carboxylic acid of Formula V as a solid. The carboxylic acid of Formula V is reduced to the benzylic alcohol of Formula VI with a ligated borane for example borane dimethylsulfide, borane dimethylamine, or borane tetrahydrofuran complex, in an aprotic solvent such as tetrahydrofuran, diethyl ether, 1,2-dimethoxyethane or methyl t-butyl ether at a temperature of from about −40° C. to about room temperature for about 1 to about 12 hours. The reaction is poured into water and the alcohol of Formula VI is isolated by extractive workup.

The compound of Formula VI is converted to an ether of Formula II by activation of the benzylic alcohol ( for example as a mesylate, tosylate, brosylate, halide) and coupling with a phenol of Formula VII. The intermediate activated derivative of Formula VI may be isolated, however a particular method is to couple the derivative of Formula VI to the phenol of Formula VII in situ. Other in situ methods for coupling the compound of Formula VII with the compound of Formula VI such as a Mitsunobu reaction can be used to form the compound of Formula II, as defined by O. Mitsunobu, *Synthesis*, 1, 1981, incorporated herein by reference.

Alternatively, the alcohol of Formula VI is treated with an alkyl or arylsulfonyl chloride or alkyl or arylsulphonic anhydride such as methanesulfonesulfonyl chloride, methanesulfonic anhydride, toluenesulfonyl chloride, or toluenesulfonic anhydride and an inorganic base such as potassium carbonate or an amine base such as triethylamine, pyridine or diisopropylethylamine in a polar aprotic solvent such as acetonitrile, pyridine, dimethylformamide, dioxane, methylene chloride, or tetrahydrofuran at a temperature of from about −50° C. to about room temperature for about 0.5 hours to about 2 hours. To the intermediate activated compound of Formula VI is added the phenol of Formula VII and the reaction is stirred at a temperature of from about room temperature to about 120° C. The product of Formula II can be isolated by adding water to the reaction mixture and collecting the resultant precipitate by filtration or by an extractive workup.

Scheme c, below, describes the conversion of a compound of Formula I to a compound of Formula VIII wherein:

$R^1$ through $R^{10}$ and Y are as given in connection with Scheme a above; and Z represents dialkyl amino, amido, alkoxy, aryloxy, acyloxy, alkylthio, arythio, acylthio, cyano, isocyano, halo and heterocycles, such as, 1,2,4-triazol-1-yl, 1,3,4-triazol-1-yl, 1,3-imidazol-1-yl, and 1,2,3,4-tetrazol-1-yl.

The compound of Formula I is dissolved in a strongly acidic medium such as a protic mineral acid, for example sulfuric acid, in the presence of a suitable nucleophile, such as 1,2,4-imiazole, at a temperature of from about 0° C. to about 110° C. for about 0.5 hours to about 48 hours. The mixture is added dropwise to water at about 0° C. and the precipitated product of Formula VIII is isolated by extractive workup or particularly by filtration.

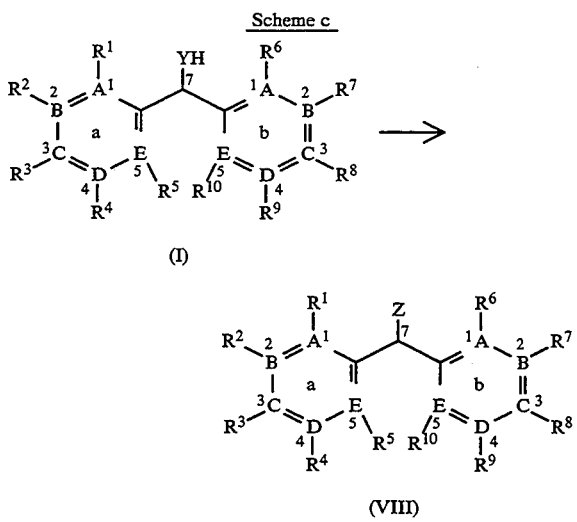

Scheme c (I)

(VIII)

EXAMPLES

In the examples that follow: "mg" means milligram(s), "M" means molar, "mL" means milliliter(s), "mmol" means millimole(s), "L" means liter(s), "mol" means mole(s), "g" means gram(s), "TLC" means thin layer chromatography, "HPLC" means high pressure liquid chromotography, "mm" means millimole(s), "mp" means melting point, "MHz" means Megahertz, "$^1$H-NMR" means proton nuclear magnetic resonance, "Hz" means Hertz, "hr" means hour(s) and "N" means normal. Also included in the following examples is terminology commonplace with the use of a proton nuclear magnetic resonance spectrometer.

Unless otherwise noted all starting materials were obtained from commercial suppliers and used without further purification. All reactions involving oxygen or moisture-sensitive compounds were performed under a dry $N_2$ atmosphere. All reactions and chromatography fractions were analyzed by thin-layer chromatography on silica gel plates, visualized with UV light and $I_2$ stain.

$^1$H-NMR spectra were measured in $CDCl_3$ or DMSO-$d_6$ using either a Varian Gemini-200 MHz or a Bruker AMX-400 MHz instrument. J values are reported in Hertz. Chemical shifts are expressed in ppm in reference to an internal standard such as $CHCl_3$ or DMSO. Apparent multiplicities are designated as s, singlet; d, doublet; t, triplet; q, quartet; m, multiplet; b, broad. AH mass spectra were taken in the positive ion mode under chemical ionization (CI), electron impact (EI), or by fast-atom bombardment (FAB). Melting points were determined on a Digital melting point apparatus, electrothermal series 1A9000, model 9200 and are uncorrected. Elemental analyses were performed by Atlantic Microlab, Norcross, Ga.

Example 1

5-[(2,6-difluoro-4-nitrophenyl)-hydroxy-methyl]-3,3-dimethyl-3H-isobenzofuran-1-one (Formula I)

A 5 L 4-necked round bottom flask is equipped with an addition funnel, gas inlet for nitrogen and thermocouple. Tetrahydrofuran (800 mL, available from Aldrich Chemical Company, Inc., 1001 West Saint Paul Avenue, Milwaukee, Wis. 53233) is transferred to the flask followed by 800 mL (0.80 mol) of 1.0 M sodium hexamethyldisilazide in tetrahydrofuran. To this yellow solution at −78° C. is added a solution of 5-(2,6-difluoro-4-nitrophenoxymethyl)-3,3-dimethyl-3H-isobenzofuran-1-one (Formula II) (140.2 g, 0.401 mol), in 700 mL of tetrahydrofuran dropwise over a 20 min. time period. During the addition the internal temperature remains below −65° C. After the addition is complete the reaction is shown to be complete by TLC and HPLC.

The reaction mixture is then poured into a 12 L extractor containing 2500 mL of methyl t-butyl ether and 2500 mL of saturated aqueous ammonium chloride solution. Solids form so an additional 500 ml of water was added which dissolve the solids. The layers are separated and the organic phase is further washed with 1200 mL each of water and brine. The organics are dried with sodium sulfate, filtered and concentrated to a yellow solid, which is dried under vacuum (1 mm, 22° C.) to yield 140 g of crude 5-[(2,6-difluoro-4-nitrophenyl)-hydroxymethyl]-3,3-dimethyl-3H-isobenzofuran-1-one. The crude product is dissolved in 450 ml of ethyl acetate on a steam bath. The resultant brown solution is chilled in an ice water bath for 20 minutes. The solids are collected by filtration and washed with hexanes and the solids are dried under vacuum; 62.57 g (44.6%) of 5-[(2,6-difluoro4-nitrophenyl)-hydroxymethyl]-3,3-dimethyl-3H-isobenzofuran-1-one are obtained as a first crop. The filtrate is concentrated to a thick slurry. The solids are isolated by filtration and washed with hexanes. After drying under vacuum (1 mm, 22° C.) 44.46 g (31.7%) of yellow solids were obtained as a second crop. The combined yield of 5-[(2,6-difluoro-4-nitrophenyl)-hydroxymethyl]-3,3-dimethyl-3H-isobenzofuran-1-one is 107.0 g (76.3%). $^1$H-NMR ($CDCl_3$, 400 MHz): δ 7.84 (m, 3H), 7.61 (s, 1H), 7.42 (d, J =8 Hz, 1H), 6.42 (d, J =7 Hz, 1H), 2.86 (d, 7 =Hz, 1H), 1.68 (s, 3 H) 1.66 (s, 3 H). Anal. Calcd for $C_{17}H_{13}N_1O_4F_2$:58.46 %C, 3.75 % H, 4.01% N; Found: 58.38% C, 3.75 % H, 3.96% N.

Example 2

2-(2,5-dimethylphenyl)-propan-2-ol (Formula IV)

A solution of 2,5-dimethylacetophenone (Formula III), available from Aldrich Chemical Company, Inc., 1001 West Saint Paul Avenue, Milwaukee, Wis. 53233, (25.5 g, 172.05 mmol) in 100 mL of diethyl ether is cooled to −20 ° C. under a nitrogen atmosphere. The contents are then treated with 3.0M methylmagnesium bromide (70 mL, 210 mmol), dropwise, at a rate which maintains the reaction temperature between about −20° and about −15° C. A white precipitate forms, which is stirred overnight at room temperature. The reaction mixture is slowly poured into cold 1.0N hydrochloric acid (200 mL), and the desired material is extracted with methylene chloride (500 mL, 150 mL). The combined extracts are concentrated and dried trader vacuum to provide 2-(2,5-dimethylphenyl)-propan-2-ol (Formula IV) (28.11 g. 171.14 mmol, 99%) as a pale-yellow, semi-solid. $^1$H-NMR ($CDCl_3$, 200 MHz): δ1.66 (s, 6H, $CMe_2$); 2.33 (s, 3H, Me); 2.55 (s, 3H, Me); 6.97 (br d J=7.5 Hz, 1H, aromatic CH); 7.06 (m, 1H, aromatic CH); 7.28 (s, 1H, aromatic CH). IR (thin film): 3400 $cm^{-1}$ (s, OH). Anal. Calcd for $C_{11}H_{16}O$: C, 80.44; H, 9.82. Found: C, 80.54; H, 9.80.

Example 3

3,3-dimethyl-1-oxo-1,3-dihydro-isobenzofuran-5-carboxylic acid (Formula V)

A mixture of 2-(2,5-dimethylphenyl)-propan-2-ol (Formula IV) (25.0 g, 152.21 mmol), prepared as in Example 2, cetyltrimethylammonium bromide (1.0 g, 2.74 retool) and potassium permanganate (61.0 g, 385.98 mmol, 2.54 eq) is slowly heated in water (150 mL). When the flask temperature reaches 70° C., an exothermic reaction to 103° C. is observed, which persists for five minutes and stabilizes at 80° C. After 2 hr, the mixture is allowed to cool to 50° C. and then filtered over Celite (42 g). The solids are washed with water (50 mL), and the combined aqueous phase is washed with methylene chloride (50 mL), cooled to 0° C., and acidified to pH 2 with concentrated HCl. A white solid is collected by filtration, and dried under high vacuum overnight to give 3,3-dimethyl-1-oxo-1,3-dihydroisobenzofuran-5-carboxylic acid (Formula V) (17.07 g, 76.68 mmol, 50%) as a white solid: mp>250° C. (dec); $^1$H-NMR (DMSO-d$_6$, 400 MHz): $\delta$1.67 (s, 6H, CMe$_2$); 7.91 (d, J=7.7Hz, 1H, aromatic CH); 8.11 (dd, J=1.2, 7.7Hz, 1H, aromatic CH); 8.31 (s, 1H, aromatic CH). Anal. Calcd for C$_{11}$H$_{10}$O$_4$.0.45 HCl: C, 59.35; H, 4.73. Found: C, 59.46; H, 4.52.

Example 4

5-hydroxymethyl-3,3-dimethyl-3H-isobenzofuran-1-one (Formula VI)

A solution of 3,3-dimethyl-1-oxo-1,3-dihydroisobenzofuran-5-carboxylic acid (Formula V) (5.0 g, 24.25 mmol), prepared as in Example 3, in anhydrous tetrahydrofuran (25 mL) is cooled to −8° C. under a nitrogen atmosphere and treated with 1.0M borane tetrahydrofuran complex (37.0 mL), dropwise, at a rate which keeps the temperature below −5 ° C. The contents are stirred overnight at room temperature, rotary evaporated, and the white solid foam is treated with ethyl acetate (50 mL). The contents are cooled to 0° C., treated with 6N HCl (100 mL), and stirred for 20 min. at room temperature. The layers are separated, and the aqueous phase is extracted with ethyl acetate (50 mL). The combine organic layers are concentrated and dried under vacuum to give 5-hydroxymethyl-3,3-dimethyl-3H-isobenzofuran-1-one (Formula VI) (4.22 g, 21.95 mmol, 90%) as a white solid: mp 59°-63° C.; $^1$H-NMR (CDCl$_3$, 400MHz): $\delta$1.69 (s, 6H, CMe$_2$); 4.89 (s, 2H, —CH$_2$—); 7.48 (m, 2H, aromatic CH); 7.85 (br d, J=8.4 Hz, 1H, aromatic CH). Mass spectrum (FAB+): m/e 193 (M+1, 100%). Anal. Calcd for C$_{11}$H$_{12}$O$_3$.0.10 H$_2$O: C, 68.10; H, 6.34. Found: C, 68.02; H, 6.30.

Example 5

5-(2,6-difluoro-4-nitrophenoxymethyl)-3,3-dimethyl-3H-isobenzofuran-1-one (Formula II)

A solution of 5-hydroxymethyl-3,3-dimethyl-3H-isobenzofuran-1-one (Formula VI) (0.55 g, 2.86 mmol) prepared as in Example 4, and pyridine (0.68 g, 8.60 mmol) in anhydrous acetonitrile (10 mL) is cooled to −16° C. under a nitrogen atmosphere. A solution of methansulfonic anhydride (0.75 g, 4.31 mmol) in anhydrous acetonitrile (10 mL) is added, dropwise, at a rate which keeps the flask temperature below −10° C. A solid precipitates during the addition, and the contents are stirred for 30 min., warmed to room temperature, and then treated with a solution of 2,5-difluoro-4-nitrophenol (0.53 g, 3.03 mmol, available from Interchem Corp, 120 Rt. 17 North, Suite 115, Paramus N.J. 07652), in anhydrous acetonitrile (5 mL). The mixture is heated to reflux under nitrogen, at which time dissolution occurs. After 90 min., the dark solution is cooled to room temperature and poured into cold water (40 mL). An off-white solid is collected by filtration and air-dried overnight to provide 5-(2,6-difluoro-4-nitro-phenoxymethyl)-3,3-dimethyl-3H-isobenzofuran-1-one (Formula II). (0.79 g, 2.26 mmol, 79%) as an off-white solid: mp 125°-127° C.; $^1$H-NMR (CDCl$_3$, 400MHz): $\delta$1.71 (s,6H, CMe$_2$); 5.48 (s, 2H, —CH$_2$—); 7.57 (m, 2H, aromatic CH); 7.91 (m, 3H, aromatic CH). Anal. Calcd for C$_{17}$H$_{13}$NF$_2$O$_5$.0.15H$_2$O: C, 58.01; H, 3.81; N, 3.98. Found: C, 57.93; 3.68; N, 3.98. Mass spectrum (EI+): m/e 349 (M+., 3%); 334 [(M−CH$_3$)+, 100%)].

Example 6

5-methanefulfonyloxymethyl 3,3-dimethyl-3H-isobenzofuran-1-one (Formula VI)

A solution of 5-hydroxymethyl-3,3-dimethyl-3H-isobenzofuran-1-one (Formula VI) (0.70 g, 3.64 mmol) and pyridine (0.83 g, 10.51mmol) in anhydrous methylene chloride (10 mL) is cooled to −15 ° C. under a nitrogen atmosphere. A solution of methansulfonic anhydride (0.95 g, 5.45 mmol) in anhydrous methylene chloride (10 mL) is added, dropwise, at a rate which keeps the flask temperature below −10° C. A solid precipitates during the addition, and the contents are stirred for 2 hr, filtered, and the filtrate is concentrated. The crude material is purified by chromatography (silica gel 60, 10% ethyl acetate/methylene chloride) to give the mesylate (0.81 g, 3.0 mmol, 82%) as a yellow, crystalline solid. $^1$H-NMR (CDCl$_3$, 400 MHz): $\delta$1.71 (s, 6H, CMe$_2$); 3.09 (s, 3H, MeSO$_3$); 5.37 (s, 2H, —CH$_2$—); 7.48 (s, 1H, aromatic CH); 7.55 (dd, J=0.73, 7.7 Hz, 1H, aromatic CH); 7.92 (d, J=7.7Hz, 1H, aromatic CH). Mass spectrum (FAB+): m/e 271 (M+1, 95%). Anal. Calcd for C$_{12}$H$_{14}$O$_5$S: C,53.32; H, 5.22; S, 11.86. Found: C, 53.40; H, 5.28; S, 11.80.

Example 7

5[(2,6-difluoro-4-nitrophenyl)-[1,2,4]triazol-1-ylmethyl]-3,3-dimethyl-3H-isobenzofuran-1-one (Formula VIII)

The diarylcarbinol (5-[(2,6-difluoro-4-nitrophenyl)-hydroxymethyl]-3,3-dimethyl-3H-isobenzofuran-1-one ((Formula I) as prepared in Example 1; 171.3 g, 0.49 moles) and 1,2,4 triazole (85.7 g, 1.24 moles) are charged into a 3L, 4-necked round bottom flask equipped with a mechanical stirrer and a nitrogen inlet. This rapidly stirred mixture is cooled in an ice bath and 680 mL of ice cold concentrated H$_2$SO$_4$ is added in one portion. After 20 min the ice bath is removed and the resultant solution is stirred at room temperature for 20 hr. The dark solution is transferred to an addition funnel and added dropwise over 3 hr to 12L of rapidly stirring ice water in a 22L, 4-necked flask, during which time 5-[(2,6-difluoro-4-nitrophenyl)-[1,2,4]triazol-1-ylmethyl]-3,3-dimethyl-3H-isobenzofuran-1-one precipitates as a fine white solid. After standing for 2 h at 0° C., the solid product is isolated by vacuum filtration, washed with H$_2$O (500 mL), and air dried for 2-12 hr. The resultant solid is transferred to a clean 3L, 4-necked flask equipped with a reflux condenser, mechanical stirrer, and J-Kem thermocouple. 1.5 L of MeOH is added, and the mixture is heated to 55 ° C. to give a dear solution. This solution is filtered while hot into a clean 3L 4-necked flask, equipped with an addition funnel, and mechanical stirrer. H$_2$O (175 mL) is then added dropwise to this rapidly stirred hot solution. As the solution cools, white crystals of 5-[(2,6-difluoro-4-nitrophenyl)-[1,2,4]triazol-1-yl-methyl ]-3,3-dimethyl-3H-isobenzofuran-1-one form. After standing at room temperature for about 2 hr to about 12 hr, the crystals are collected by filtration, air dried for 3 hr, and then dried under vacuum to afford 132.2 g (67 %) of 5-[(2,6-difluoro-4-nitrophenyl)-[1,2,4]triazol-1-yl-methyl]-3,3-dimethyl-3H-isobenzofuran-1-one which is >98% pure by HPLC analysis.

This material was combined with of a total of 604.6 g of separate batches of 5-[(2,6-difluoro-4-nitrophenyl)-[1,2,4]triazol-1-yl-methyl]-3,3-dimethyl-3H-isobenzofuran-1-one prepared by this same procedure and charged into a 12L, 4-necked round-bottom flask equipped with a reflux condenser, mechanical stirrer, and a J-Kem thermocouple. 6.4 L of MeOH is added, and the mixture is heated to 60° C. to afford a clear solution. Delcolorizing charcoal (DARCO, 10.24 g) is added, the mixture is stirred at 60° C. for 10 min, and then filtered while hot into a clean 12L ,4-necked flask equipped with a mechanical stirrer and addition funnel. Water (960 mL) is then added dropwise to this rapidly stirred hot solution. As the solution cools, white crystals of 5-[(2,6-difluoro-4-nitrophenyl)-[1,2,4]triazol-1-yl-methyl]-3,3-dimethyl-3H-isobenzofuran-1-one form. After standing at room temperature for 2 hr, the crystals are collected by filtration, air dried for 3 hr, and then dried under vacuum for 48 hr to afford 453.5 g of 5-[(2,6-difluoro-4-nitrophenyl)-[1,2,4]triazol-1-yl-methyl]-3,3-dimethyl-3H-isobenzofuran-1-one as an off-white powder which was >99 % pure by HPLC analysis: m.p. 163.3–163.7° C.; $^1$H NMR (400 MHz, DMSO-d$_6$) δ1.54 (s, 3H), 1.56 (s, 3H), 7.17 (d, J=8.1 Hz, 1H), 7.54 (s, 1H), 7.66 (s, 1H), 7.81 (δ, J=8.0 Hz, 1H), 8.12–8.15 (m, 3H), 8.72 (s, 1H); Analysis calcd for C$_{19}$H$_{14}$N$_4$O$_4$F$_2$: C, 57.00; H, 3.52; N, 13.99; found: C, 56.81; H, 3.49; N, 13.93.

What is claimed is:

1. A method of synthesizing a diarylmethane of the following Formula (I):

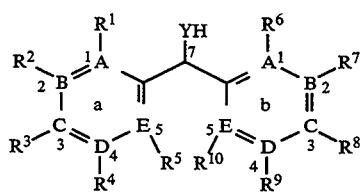

wherein:
Y is oxygen or sulfur;
A, B, C, D, and E are carbon or 1, 2 or 3 of A, B, C, D, and E are independently nitrogen, and the others are carbon; and wherein
R$^1$ through R$^{10}$ are selected independently from the group consisting of: hydrogen, hydroxy, alkyl, C$_3$-C$_8$ cycloalkyl, C$_3$-C$_8$ cycloalkyl alkyl, alkenyl, hydroxy alkyl, alkoxy alkyl, perhalo-alkyl, amino, nitro, nitrile, halo oxo, carboxyl, sulfonyl, acyl, formyl, carbamoyl, trifluoromethyl, aminomethyl, azido, amido, hydrazino, aryl, aryloxy, heteroaryl, or aryl or heteroaryl, mono, di, or tri substituted with one or more hydrogen, hydroxy, alkyl, C$_3$-C$_8$ cycloalkyl, C$_3$-C$_8$ cycloalkyl alkyl, alkenyl, hydroxy alkyl, alkoxy alkyl, perhaloalkyl, amino, nitro, nitrile, halo, carboxyl, sulfonyl, acyl, formyl, carbamoyl, trifluoromethyl, aminomethyl, azido, amido, hydrazino, aryl, aryloxy, or heteroaryl groups and the pharmaceutically acceptable salts and solvates thereof; and wherein;
adjacent substitutents on either the "a" ring or "b" ring may be joined together to form a fused ancillary 5 or 6 atom carbocyclic or heterocyclic ring structure wherein substitutents on the ancillary ring structure may each independently be as represented for R$^1$ through R$^{10}$ above and the pharmaceutically acceptable salts and solvates thereof;

comprising reacting:
i) an ether of the following Formula (II):

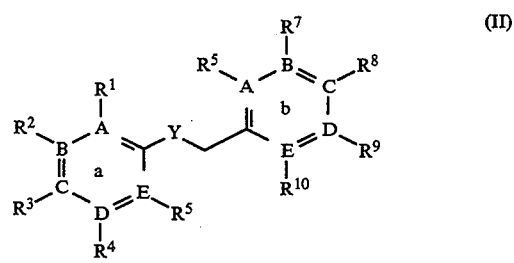

wherein
R$^1$ through R$^{10}$ are as described above; and
ii) alkali metal amide base or alkali metal alkoxy base.

2. The method of claim 1, wherein the alkali metal amide or alkoxy base is selected from the group consisting of: potassium tert-butoxide, lithium diisopropylamide and sodium hexamethyldisilazide.

3. The method of claim 2, wherein the alkali metal amide base is sodium hexamethyldisilazide.

4. The method of claim 3, wherein the reaction takes place in a polar aprotic solvent selected from the group consisting of: dimethylfomamide, diethyl ether methyl t-butyl ether and 1,2, dimethoxyethane.

5. The method of claim 4, wherein the polar aprotic solvent is tetrahydrofuran.

6. The method of claim 5, wherein the reaction takes place at a temperature of from about −78° C. to about 50° C.

* * * * *